United States Patent [19]

Harris

[11] 4,401,434
[45] Aug. 30, 1983

[54] KIT ADAPTED TO FACILITATE STORAGE AND USE OF SPLINTER-REMOVING MATERIALS

[76] Inventor: Jeanette C. Harris, 1636 N. Wells St., Chicago, Ill. 60614

[21] Appl. No.: 275,639

[22] Filed: Jun. 22, 1981

[51] Int. Cl.³ .............................................. A61F 17/00
[52] U.S. Cl. ................................... 604/310; 128/354; 206/570
[58] Field of Search ........................ 128/354, 269, 272; 206/438, 363, 570, 803; 81/43; 604/195, 310; 132/79 R, 79 A, 79 B

[56] References Cited

U.S. PATENT DOCUMENTS 2,451,994  10/1948  Towns ............................ 128/354 X
2,803,252  8/1957  Bloome ........................... 128/354 X

FOREIGN PATENT DOCUMENTS 101275  9/1923  Switzerland ....................... 128/354

Primary Examiner—Michael H. Thaler
Attorney, Agent, or Firm—James T. FitzGibbon

[57] ABSTRACT

A kit containing equipment and medication to facilitate the removal of slivers or similar foreign substances from the human body. The kit includes a receptacle, adapted to be filled with an antiseptic or similar fluid, and a cap positionable over the receptacle in a fluid-tight relation. The cap includes a fluid applicator and a view enlarging assembly hingedly connected to the top section of the cap. The cap is also equipped with splinter removal equipment including a pair of tweezers and a needle.

5 Claims, 5 Drawing Figures

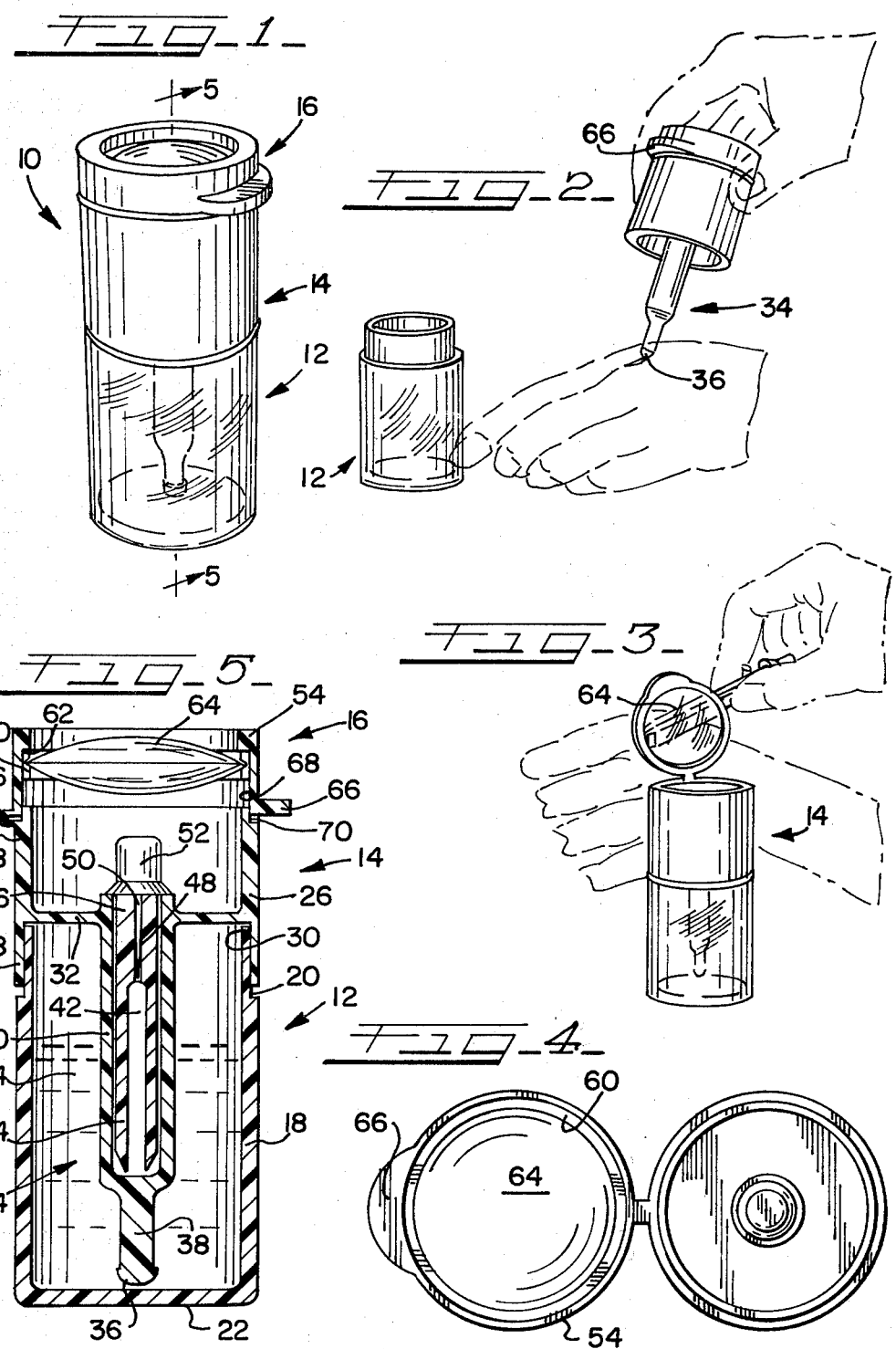

KIT ADAPTED TO FACILITATE STORAGE AND USE OF SPLINTER-REMOVING MATERIALS

The present invention relates generally to specialty packages or kits, and more particularly, to a composite kit which includes all materials necessary for identifying, disinfecting and removing splinters or the like from the body, particularly, such as, for example, splinters from the fingers of children or the like.

One of the most common minor injuries suffered by children and adults is that of receiving a splinter or the like in the finger or other body part. Very commonly, such splinters are received from toys, play things, furniture or other wooden articles, and occasionally from metal articles or the like. In addition, other splinters, such as those of glass, plastic or the like are often embedded in the finger of a person as a result of work, play or other activity. Similar problems are posed by insect stingers, thorns from bushes, and the like.

While such injuries, in and of themselves, are not of major importance, they are often annoying, particularly when located in a sensitive region, such as the hand or finger, wherein minor pain serves to render the hand or finger useless for writing or other fine muscle manipulation.

In addition, certain splinters, insect stingers, thorns or the like are often contaminated, or are in and of themselves poisonous or contaminated with bacteria, leading to the possibility that a moderate or even severe infection may develop if the affected body part is not treated properly.

Historically, the removal of a splinter, although requiring a certain amount of dexterity and technique, is not a difficult problem, and usually involves the application of an antesptic, the removal of surrounding skin by a needle or the like, and subsequent removal of the splinter, thorn or the like itself with the needle and/or a pair of tweezers provided for this purpose.

However, the difficulty in removing the splinter often arises because the materials for identifying it in the hand are not readily available, and because removal of the splinter involves manipulating several instruments at the same time. Ideally, treatment of a splinter calls for applying an antiseptic to the affected area, identifying the foreign matter by a dye which will cause it to stand out by contrast from the surrounding area, then, with the aid of a magnifying glass, manipulating the needle and/or tweezers in such a way as to open up the passage through which the splinter entered the skin, and then removing it with the needle, tweezers, or both.

As commonly as splinters occur, there still has not been provided a unitary kit which would provide all the equipment and materials needed to remove a splinter, and which would be available at low cost while providing convenience of assembly, storage, retention, and positioning of the required components.

In view of the failure of the prior art to provide an economical and convenient kit for this purpose, it is an object of the present invention to provide an improved splinter removal kit.

Another object of the invention is to provide a kit which includes a magnifying or like viewing glass, splinter removal equipment, typically comprising a needle and tweezer assembly, means for storing these units, a well or like receptacle for an antiseptic, preferably one which contains a die, and an applicator for the antiseptic.

Yet another object of the invention is to provide a kit which is adapted for easy storage, and which will maintain all the components needed for splinter treatment and removal in a single location, and which is further adapted to store its contents for an indefinite period.

A still further object of the invention is to provide a splinter identification, treatment, and removal kit which includes a convenient antiseptic applicator, a needle and tweezers unit, a storage area therefore, and an antiseptic storage receptacle.

A further object is to provide a kit which will be easy to manufacture and market, and which will be able to be merchandised attractively.

Another object of the invention is to provide a kit which includes one or more medicaments, and the potential to be refilled therewith as a convenience for the user, and as a marketing incentive for the seller of such medicinal products.

A still further object of the invention is to provide a unitary kit having all necessary equipment for identifying a sliver, treating the affected area, and removing the splinter, and which further includes a magnifying glass or other viewing aid as well as means for positioning the viewing aid adjacent the affected area to free both hands of the person applying the treating for manipulating the instruments used in sliver removal.

A still further object is to provide a splinter identification and treatment kit having a sight glass element forming the cover portion of the kit and permanently affixed thereto by an integral hinge, such as a polypropylene hinge and adapted to maintain the viewer in a position adjacent the affected portion of the patient.

The foregoing and other objects and advantages of the invention are achieved in practice by providing a sliver identification, treatment and removal kit which includes storage areas for a medicinal preparation, for one or more removal instruments, and a viewing aid for observing the affected area.

The exact manner in which the foregoing and other objects and advantages are achieved in practice will become more clearly apparent when reference is made to the accompanying detailed description of the preferred embodiments of the invention set forth by way of example and shown in the accompanying drawings, in which like reference numbers indicate corresponding parts throughout.

BRIEF DESCRIPTION OF THE DRAWINGS

FIG. 1 is a perspective view of the kit of the invention, showing the same in the closed or assembled relation;

FIG. 2 is a perspective view of the kit of the invention in partially disassembled form, and showing the user applying the antiseptic to the hand of the victim;

FIG. 3 is a perspective view similar to that of FIG. 2 but showing the use of the captive magnifying glass portion of the splinter treatment and removal kit;

FIG. 4 is a top plan view of the kit of FIGS. 1-3, showing the same with the top open and the magnifying glass portion connected to the upper part of the kit by an integral hinge mechanism; and FIG. 5 is a vertical sectional view, taken along lines 5—5 of FIG. 1, and showing, on an enlarged scale, the essential components of the invention.

BRIEF DESCRIPTION OF THE PREFERRED EMBODIMENTS OF THE INVENTION

While the invention is capable of being embodied in different forms, a preferred form thereof will be shown and described wherein the unit includes a receptacle for receiving an antiseptic, means for holding and positioning the antispetic applicator, and for positioning the magnifying glass and the splinter removal equipment.

Referring now to FIG. 1, the invention is to be embodied in a kit generally designated 10 and shown to include an antiseptic receptacle portion generally designated 12, an intermediate or treatment and removal equipment portion 14 and an upper, combination cover and view-enlarging portion 16.

Referring now to FIG. 5, certain of these elements are shown in greater detail. Thus, the antiseptic receptacle portion 14 is shown to include a generally cylindrical sidewall 18 having a reduced diameter upper neck portion 20 and a bottom wall 22. This receptacle is adapted to contain a supply of a liquid 24 of the type adapted to disinfect the area of the body having the spinter embedded therein, and to dye the splinter or otherwise provide contrast between the splinter and the surrounding skin area. A flourescent dye or the like, of a type known to those skilled in the art, is preferably disposed in the antispetic, such as a mercurochrome or iodine solution, for this purpose.

Referring now to the intermediate portion of the kit, the section 14 is shown to include a medicine applicator handle in the form of a generally cylindrical sidewall portion 26, having a downwardly extending skirt 28 with inwardly directed sidewalls 30, adapted to be received with a slight press fit over the reduced diameter neck section 20 of the receptacle 12.

In addition to the sidewall 26, the handle or intermediate section 14 includes a web 32 extending radially inwardly from the sidewalls 26. Received centrally of the web 32 and extending transversely of the center thereof is a combination instrument receiver and applicator stem 34. As shown, the assembly 34 includes a tip 36 at the end of a lower shank portion 38. An enlarged diameter portion 40 of the applicator-receiver 34 includes a hollow center section 42 which is adapted to receive a pair of tweezers 44 therein.

As shown, the head portion 46 of the tweezers 44 has therein an axially extending opening 48 which receives the shank portion 50 of a pin 52. The tweezers 44 and pin 52 may be removed as a unit, or separately, from the opening 42 in the receiver portion 40 of the applicator-receiver 34, as will appear.

The view enlarging portion 16 of the kit 10 includes a captive cap 54 which is tethered by an integral hinge 56 to an upper portion 58 of the handle 26. A gasket 60 which engages a shoulder 62 on the cap 54, positions view enlarging means in the form of a lens 64 within the cap 54. A finger tab 66 is provided for ease in removing the cap, which is also lightly press fit at the lower part of its inner diameter 68 over a reduced diameter neck 70 at the top of the handle 26.

Referring now to the use of the instrument, reference is made to FIGS. 2 and 3. It will be assumed that the victim has a sliver embedded in the central part of his hand, and further assumed that the receptacle 12 contains a liquid combination disinfectant and dye such as an alcohol solution of Mercurochrome, preferably with a fluorescent dye therein. After the injury has occurred, the user removes the handle 26 and its captive cap assembly 54 from the receptacle 12, and manipulates it as a unit to insure that the applicator 26 is immersed in the solution 24.

Thereupon, the area of the sliver is contacted with the applicator tip 36 until the area is disinfected and the sliver is highlighted visually by the dye. Then, the user removes the instruments and positions the handle 26 over the receptacle 12 by mutual engagement of the portions 20, 30. With the intermediate or handle section 26 thus being fixed with respect to the receptacle, the tab 64 is lifted and the lens 64 is positioned by manipulating the integral hinge 56 to the position of FIG. 3, or other suitable position.

At this point, the pin 52 may be removed and utilized to pull the skin away from the sliver in the entrance area, exposing the end of the sliver. The use of the magnifying glass assists in this operation and its ability to be held in place by the hinge is particularly useful if two hands are needed to manipulate the instruments.

Assuming that the sliver remains embedded in the skin, the tweezers 44 is then manipulated in a known manner so as to remove the sliver. Thereafter, additional antiseptic may be applied if desired. After use, the instruments may be replaced in the instrument receptacle, and the entire kit reassembled to await further use.

While the mounting of the intermediate or applicator section 26 with respect to the liquid receptacle portion 12 has been shown to be a pair of cooperating cylindrical surfaces 20, 30 having a light press fit relation, it is anticipated that the association between these parts may be accomplished by providing mutually engaging threads on the cooperating portions 20, 30, and that these parts may be secured together with or without a gasket, O-ring or other known seal means.

While the exact materials used in making the kit of the invention do not form an essential aspect of the invention, an advantage of the kit is that economical materials may be used in its construction. For example, the liquid receptacle 12 is preferably made from a clear, blow molded plastic material so that the supply of antiseptic therein can be viewed.

The dauber or applicator 38 may be of a plastic material, or may have a rubber, felt or bristle tip (not shown). The intermediate or instrument receptacle portion 34 may likewise be conveniently made of a plastic, such as an injection molded thermoplastic or thermosetting resin. The pin 52 preferably has an enlarged head portion, with the shank 50 and tip being preferably made from stainless steel or chromium plated steel. The tweezers 44 may also be made of plastic or metal, and if made from plastic, should be made from a hard material, at least in the tip area. The lens 64 may be made from glass or plastic, as desired.

In addition to the advantages of containing all the necessary equipment for locating and removing slivers, the kit of the invention also has other advantages. For example, making the hinge 56 from a plastic material, such as polypropylene, provides an indefinite service life for the hinge and also makes the hinge sufficiently stiff so that the lens may be retained in position of use to assist the user in viewing the affected area. Still further, the unit may be used as a promotional package or article, whereby the manufacturer of the antiseptic or similar consummable product may wish to furnish the kit at low cost, or reduced cost, as a manner of inducing repurchase of such promoted product.

In this connection, the kit may also serve as a reminder to purchase other personal or health care products of the same company, such as bandages, medicines, etc.

While the concentric, axially aligned position of the applicator tweezers and pin is a preferred and convenient way of arranging the components of the kit, other convenient arrangements may also be made without departing from the spirit of the invention.

It will thus be seen that the present invention provides a novel sliver removal kit having a number of advantages and characteristics, including those pointed out above, and others which are inherent in the invention. A preferred embodiment of the invention having been described by way of illustration, it is anticipated that changes and modifications of the kit will occur to those skilled in the art, and that such changes and modifications may be made without departing from the spirit of the invention or the scope of the appended claims.

I claim:

1. A kit containing equipment and medication adapted to facilitate removal of slivers or like foreign substances from the human body, said kit comprising, in combination, a fluid receptacle and means forming a part thereof for receiving a cap thereover in fluid tight relation, a cap unit for said fluid receptacle, said cap unit including a fluid applicator and an instrument-receiving portion forming a part thereof, at least one splinter removal instrument detachably disposed in said instrument receiving portion of said cap, and a view enlarging assembly having a portion thereof adapted to be received and secured over said cap unit in overlying relation to said instrument-receiving portion of said cap.

2. A kit containing equipment and medication adapted to facilitate removal of sliver or like foreign substances from the human body, said kit comprising, in combination, a fluid receptacle defined by bottom and sidewall portions and having an open top portion, a combination fluid applicator and splinter removal instrument receptacle, said combination applicator and receptacle including a portion adapted to serve as a handle for the applicator and a portion adapted to act as the cover for said open top portion of said liquid receptacle, cooperating means on said handle portion and said open top portion of said fluid receptacle so as to provide a fluid-tight fit therebetween, at least one instrument detachably received in said instrument receptacle, and a magnifying lens assembly associated with said combination applicator and instrument receptacle, said magnifying lens assembly being attached to said applicator and receptacle by an integral hinge capable of supporting said lens in a desired position of use.

3. A kit as defined in claim 2, wherein said fluid receptacle is made from a transparent plastic material.

4. A kit as defined in claim 2, wherein said applicator portion of said applicator and receptacle assembly comprises the lower end portion of a generally cylindrical housing having a central passageway extending axially thereof, with said instrument being received within said central passageway.

5. A kit as defined in claim 2, wherein said at least one instrument comprises a sliver removing pin unit and a pair of tweezers.

* * * * *